United States Patent [19]
Manis et al.

[11] Patent Number: 4,647,683
[45] Date of Patent: Mar. 3, 1987

[54] PREPARING ESTER CONTAINING ORGANOSILICON COMPOUNDS

[75] Inventors: Paul A. Manis, Allentown, Pa.; Eugene R. Martin, Onsted, Mich.

[73] Assignee: (SWC) Stauffer-Wacker Silicones Corporation, Adrian, Mich.

[21] Appl. No.: 845,146

[22] Filed: Mar. 27, 1986

[51] Int. Cl.$^4$ ............................ C07F 7/08; C07F 7/18
[52] U.S. Cl. .................................................. 556/440
[58] Field of Search ............ 556/440; 260/410, 410.5, 260/410.9 R

[56] References Cited

U.S. PATENT DOCUMENTS

| | | | |
|---|---|---|---|
| 2,770,632 | 11/1956 | Merker | 556/440 |
| 2,770,633 | 11/1956 | Sommer | 556/440 |
| 2,833,802 | 5/1958 | Merker | 556/440 |
| 3,494,950 | 2/1970 | Simmler et al. | 556/440 |

Primary Examiner—Paul F. Shaver

[57] ABSTRACT

An improved process for preparing ester containing organosilicon compounds by reacting chloro-organosilicon compounds with a carboxylic acid in the presence of a base and a promoting solvent, the improvement which comprises conducting the reaction in the presence of a halide salt.

10 Claims, No Drawings

PREPARING ESTER CONTAINING ORGANOSILICON COMPOUNDS

The present invention relates to ester containing organosilicon compounds and more particularly to an improved process for preparing ester containing organosilicon compounds.

BACKGROUND OF THE INVENTION

Organosilicon compounds containing ester groups are described in U.S. Pat. No. 2,956,044 to Merker in which an acryloxymethyl substituted organosilicon compound is prepared by reacting the corresponding chloromethyl substituted organosilicon compounds and acrylic acid or methacrylic acid in the presence of a tertiary amine.

Also, U.S. Pat. No. 2,793,223 to Merker discloses a method for preparing acryloxymethyl substituted organosilicon compounds by reacting a metal salt of acrylic or methacrylic acid with the corresponding chloromethyl substituted organosilicon compounds in the presence of a mutual solvent such as dimethylformamide.

U.S. Pat. No. 4,348,454 to Eckberg discloses a method for preparing acrylic functional silicone polymers by reacting omega-chloroalkylmethyl silicone fluids with acrylic acid or methacrylic acid in the presence of a tertiary amine base such as triethylamine or pyridine.

It has been found that improved yields of ester containing organosilicon compounds are obtained when a chlorosubstituted alkyl silicon compound is reacted with a carboxylic acid in the presence of a halide salt and a solvent which promotes the reaction.

Therefore, it is an object of the present invention to provide an improved process for preparing ester containing organosilicon compounds. Another object of the present invention is to provide an improved process for preparing ester containing organosilicon compounds in the presence of a catalyst. Still another object of the present invention is to provide an improved process for preparing ester containing organosilanes and organopolysiloxanes. A still further object of the present invention is to provide ester containing organosilicon compounds which will cure in the presence of ultraviolet radiation.

SUMMARY OF THE INVENTION

The foregoing objects and others which will become apparent from the following description are accomplished in accordance with this invention, generally speaking, by providing an improved process for preparing ester containing organosilicon compounds by reacting a chloro-substituted alkyl organosilicon compound with a carboxylic acid in the presence of a base, and a promoting solvent, if desired, the improvement which comprises conducting the reaction in the presence of a catalytic amount of a halide salt.

DESCRIPTION OF THE INVENTION

Organosilicon compounds which may be employed in the process of this invention are chloro-substituted organosilanes of the formula $$(Cl-R'')_a SiR_{3-a}$$

and chloro-substituted organopolysiloxanes of the formula

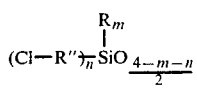

where R, which may be the same of different is a monovalent hydrocarbon radical having from 1 to 20 carbon atoms or a hydrocarbonoxy radical of the formula OR', in which R' is a monovalent hydrocarbon radical having from 1 to 20 carbon atoms, R'' is a divalent saturated hydrocarbon radical having from 1 to 20 carbon atoms, a is a number of from 1 to 4, m is a number of from 1 to 2 and n is a number of from 1 to 2.

Other siloxane units which may be present in the organopolysiloxanes are those of the formula

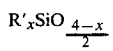

where R' is the same as above and x is an integer of from 1 to 3.

Examples of monovalent hydrocarbon radicals represented by R and R' are alkyl radicals, such as the methyl, n-propyl, isopropyl, butyl, hexyl, octyl and decyl radicals, as well as the octadecyl radicals; alkenyl radicals such as the vinyl and the allyl radicals; cycloaliphatic hydrocarbon radicals such as the cyclopentyl and the cyclohexyl radicals, as well as methylcyclohexyl and cyclohexenyl radicals; aryl radicals such as the phenyl and xenyl radicals; aralkyl radicals such as the benzyl, beta-phenylethyl and the beta-phenylpropyl radicals and alkaryl radicals such as the tolyl radicals.

Examples of suitable divalent radicals represented by R'' are alkylene radicals such as ethylene, trimethylene, tetramethylene, hexamethylene, octamethylene and eicosamethylene radicals. The preferred divalent radicals are alkylene radicals having from 1 to 6 carbon atoms.

Examples of suitable hydrocarbonoxy radicals represented by OR' are methoxy, ethoxy, propoxy, butoxy, hexoxy, octoxy, decoxy, octadecoxy and phenoxy radicals.

Examples of preferred chloro-substituted alkyl organosilanes which may be employed in this invention are silanes such as chloromethyltrimethylsilane, chloroethyltriethylsilane, 3-chloropropyltrimethylsilane, chlorobutyltrimethylsilane, chloroethyltrimethylsilane, 3-chloropropyltributylsilane, 3-chloropropyltrimethoxysilane, 3-chloropropylmethyldimethoxysilane and 3-chloropropyltrioctoxysilane.

Examples of preferred chloro-substituted organopolysiloxanes are organopolysiloxanes which are endblocked with groups such as chloromethyl, 2-chloroethyl, 3-chloropropyl, 4-chlorobutyl and 8-chlorooctyl groups.

Preferred examples of chloro-substituted organopolysiloxanes are hydroxyl endblocked chloro-substituted diorganopolysiloxanes, trialkylsiloxy- or triarylsiloxy endblocked chloro-substituted dialkylpolysiloxanes, diarylpolysiloxanes, alkylarylpolysiloxanes and copolymers thereof.

Specific examples of preferred organopolysiloxanes are hydroxy endblocked or trimethylsiloxy endblocked chloromethyl and dimethyl polysiloxane copolymers, triethylsiloxy endblocked chloroethyl and diethylpolysiloxane copolymers, trimethylsiloxy endblocked omega chloropropyl methyl and dimethyl polysiloxane copolymers, trimethylsiloxy endblocked chloro-methyl and diphenyl polysiloxane copolymers, and dimethyl polysiloxane copolymers.

It is possible to use mixtures consisting of various diorganopolysiloxanes having different molecular weights and organic groups linked to the silicon atoms in preparing the compositions of this invention.

The viscosity of the chloro-substituted alkyl organopolysiloxanes may range from about 5 to 500,000 mPa.s and more preferably may range from about 50 to 100,000 mPa.s at 25° C.

Carboxylic acids which are reacted with the chloro-substituted alkyl organosilicon compounds may be represented by the formula $$R'''(COOH)_y$$

where $R'''$ is a saturated or unsaturated hydrocarbon radical having up to 20 carbon atoms and y is 1, 2 or 3.

Examples of preferred hydrocarbon radicals represented by $R'''$ are alkyl radicals such as the methyl, ethyl, n-propyl, isopropyl, butyl, hexyl, octyl and decyl radicals as well as the octadecyl radicals; alkenyl radicals such as the vinyl and the allyl radicals; cycloaliphatic hydrocarbon radicals such as the cyclopentyl and cyclohexyl radicals as well as methylcyclohexyl and cyclohexenyl radicals; aryl radicals such as the phenyl, xenyl and anthryl radicals; aralkyl radicals such as the benzyl, beta-phenylethyl and the beta-phenylpropyl radicals and alkaryl radicals such as the tolyl and xylyl radicals.

Other examples of suitable hydrocarbon radicals represented by $R'''$ are hydrocarbon radicals such as ethylene, trimethylene, tetramethylene, hexamethylene, octamethylene, dodecylmethylene, vinylene, propenylene, butylene, xenylene and butadienylene radicals.

Examples of suitable monocarboxylic acids which may be employed are formic acid, acetic acid, propionic acid, butyric acid, valeric acid, hexanoic acid, heptanoic acid, octanoic acid, undecanoic acid, lauric acid, myristic acid, pentadecanoic acid, palmitic acid, stearic acid, nonadecanoic acid and eincosanoic acid.

Examples of unsaturated monocarboxylic acids which may be employed are acrylic acid, methacrylic acid, crotonic acid, 3-butenoic acid, 3-methylcrotonic acid, 3-hexenoic acid, sorbic acid, 2-tetradecenoic acid and 2-methylene butyric acid.

Aromatic carboxylic acids which may be employed are benzoic acid, 2-naphthoic acid, 1-anthroic acid.

Polycarboxylic acids which may be employed are oxalic acid, malonic acid, succinic acid, glutaric acid, maleic acid, fumaric acid, glutaconic acid, adipic acid, pimelic acid, suberic acid, sebacic acid, dodecanedioic acid, undecanedioic acid, 1,2,3-propane tricarboxylic acid, 1,1,5-pentane tricarboxylic acid, 1,2,4-hexane tricarboxylic acid, 1,2,4-pentane tricarboxylic acid, 5-octene-3,3,6-tricarboxylic acid, phthalic acid, isophthalic acid, terephthalic acid, 1,3,5-benzenetricarboxylic acid, 1,4-cyclohexanedicarboxylic acid, naphthalic acid, 2-carboxylic-5-hydroxycinnamic acid and itaconic acid.

Catalysts which may be employed to accelerate the formation of the esters of this invention are halide salts such as alkali metal halides, ammonium halides, tertiary amine hydrohalides and quaternary ammonium halides, in which the halide is iodide or bromide. Examples of suitable alkali metal halides are sodium iodide or bromide, potassium iodide or bromide and lithium iodide or bromide. Examples of ammonium halides are ammonium iodide and bromine. Suitable examples of trialkyl ammonium halides are trimethyl and triethyl ammonium iodide or bromide. Examples of quaternary ammonium halides are tetramethyl ammonium iodide or bromide and tetraethyl ammonium iodide or bromide.

The amount of catalyst is not critical and may be as low as 0.001 equivalents of catalyst per equivalent of chlorine present on the organosilicon compound. It is preferred that an amount of from about 0.05 to about 3 equivalents of catalyst be present per equivalent of chlorine present on the organosilicon compound. More preferably, from about 0.1 to about 1.5 equivalents of catalyst may be used per equivalent of chlorine present on the organosilicon compound in the reaction.

The amount of carboxylic acid employed in the reaction with the chloro-substituted alkyl organosilicon compound may vary over a wide range. However, it is preferred that at least one equivalent of carboxylic acid be present for each equivalent of chlorine present on the chloro-substituted alkyl organosilicon compound in order to ensure that no chloro-substituted alkyl functionality remains. More preferably, the amount of carboxylic acid may range from about 1 to about 5 equivalents of carboxylic acid per equivalent of chlorine present on the chloro-substituted alkyl organosilicon compound.

When a carboxylic acid is reacted with the chloro-substituted alkyl organosilicon compound it is preferred that the reaction be conducted in the presence of a hydrogen acceptor such as an organic or inorganic base. Examples of suitable bases which may be employed in the reaction are tertiary amines of the formula $$R_3^1 N$$

where $R^1$ is a monovalent hydrocarbon radical having from 1 to 18 carbon atoms. Examples of suitable monovalent hydrocarbon radicals represented by $R^1$ are alkyl radicals such as the methyl, ethyl, n-propyl, isopropyl, butyl, octyl, decyl and octadecyl radicals; aryl radicals such as the phenyl radical; aralkyl radicals such as the benzyl, beta-phenylethyl and the beta-phenylpropyl radicals and alkaryl radicals such as the tolyl radicals as well as the cycloaliphatic radicals such as the cyclohexyl radical.

The $R^1$ radical may also be a cyclic radical in which the nitrogen atom is a substituent on the ring. Examples of such radicals are the pyrimidinyl, pyridazinyl, pyrazinyl, pyridyl and quinolyl radicals.

Examples of suitable amines are triethylamine, tripropylamine, tributylamine, quinoline, pyridine, pyrimidine and pyridazine.

Inorganic bases which may be employed are the alkali metal carbonates, alkali metal bicarbonates and alkali metal phosphates. Specific examples of alkali metal carbonates are sodium carbonate, potassium carbonate and lithium carbonate. Examples of suitable alkali metal bicarbonates are sodium bicarbonate, lithium bicarbonate and potassium bicarbonate. Alkali metal phosphates which may be employed are sodium phosphate and potassium phosphate. It is preferred that the alkali metal carbonates and phosphates be employed in the process of this invention.

Other inorganic bases which may be employed are, for example, ammonium carbonate, ammonium bicarbonates and ammonium orthophosphate.

The amount of base present in the reaction may vary over a wide range; however, it is preferred that about 1 mole of base be employed per mole of hydrogen chloride formed as by-product. More preferably, from about 1 to 3 moles of base may be present per mole of hydrogen chloride formed as a by-product of the reaction.

In addition to the catalyst and base employed in the reaction between the chloro-substituted alkyl organosilicon compound and the carboxylic acid, it is preferred that the reaction be conducted in the presence of a promoting solvent. Examples of suitable promoting agents which may be employed in the reaction are tetrahydrofuran, N-methyl-2-pyrrolidone, formamide, N,N-diethylformamide, N,N-dimethylformamide, N-ethylformamide, N-methylformamide, hexalmethyl phosphoramide and dimethyl sulfoxide. It is possible that the tertiary amine may also be a promoting solvent for the reaction.

The amount of promoting solvent employed in the reaction is not critical and may vary over a range of from about 1 to about 50 percent by weight based on the weight of the reactants, and more preferably may range from about 5 up to about 25 percent by weight based on the weight of the reactants.

The reaction may be conducted at any temperature ranging from about 30° C. up to about 200° C. over a period of time of from about 0.5 hours up to about 100 hours, and more preferably at a temperature of from about 60° C. up to about 180° C. for from about 10 to 40 hours. Obviously, the reaction time is determined primarily by the temperature at which the reaction is conducted, i.e., the lower the temperature the longer the reaction time.

The reaction may be conducted at atmospheric pressure or at pressures above or below atmospheric pressure; however, the reaction is preferably conducted at atmospheric pressure in an inert atmosphere.

The ester-containing organosilicon compounds are preferably prepared by reacting a chloro-substituted alkyl organosilicon compound with a carboxylic acid in the presence of a base, catalyst and a promoting solvent, if desired, at a temperature of from about 30° to 200° C. for from 10 to 40 hours at atmospheric pressure. The resultant ester-containing organosilicon compounds may be separated from the halide salt by-product by filtration.

When the carboxylic acid contains aliphatic unsaturation, then it is preferred that the reaction be conducted in the presence of a polymerization inhibitor such as hydroquinone or para-methoxyphenol.

A carboxylic acid salt may be used in preparing the ester-containing organosilicon compounds instead of the carboxylic acid and a base. The carboxylic acid salt is prepared by premixing the carboxylic acid with a base and then the resultant salt is combined with the chloro-substituted alkyl organosilicon compound, catalyst and promoting solvent, if desired.

The ester-containing organosilicon compounds prepared in accordance with this invention may be used as lubricating fluids, as molding and impregnating materials, as electrical insulating materials and in water-repellent treatments. When the ester-containing organosilicon compounds contain aliphatic unsaturation, they may be used as coating agents, as impregnating and molding materials, as adhesives and as bonding agents.

These ester-containing organosilicon compounds containing aliphatic unsaturation may be cured by exposure to nonionizing radiation such as ultraviolet light or by heat. When the compositions are to be cured by exposure to radiation, then it is preferred that a photosensitizer be incorporated in the composition.

Photosensitizers which may be employed are benzophenone, xanthone, thioxanthone, 2-chloro-thioxanthone, benzoin isopropyl ether, benzoquinone, 1-chloroanthraquinone, p-diacetylbenzene, 9,10-dichloroanthracene, 4,4-dichlorobenzophenone, 1,3-diphenyl-2-propane, 1,4-naphthyl-phenyl ketone, 2,3-pentanedione, mixtures of benzophenone and tertiary amines, such as N,N-dimethylethanol amine and diazo compounds which dissociate into free radicals, such as N,N-azo-bisisobutyronitrile.

The photosensitizers are generally used in an amount up to about 20 percent by weight and more preferably, the photosensitizers are present in an amount of from about 0.5 to about 5 percent by weight, based on the weight of the composition.

The ester-containing organosilicon compounds of this invention having aliphatic unsaturation may also be thermally polymerized by adding an organic peroxide in an amount of from about 0.1 to about 10 percent by weight based on the weight of the composition.

Examples of suitable organic peroxides are benzoyl peroxide, dibenzoyl peroxide, di-t-butyl peroxide, t-butylbenzoyl peroxide, cumene hydroperoxide, dicumyl peroxide, lauroyl peroxide, α-α'-bis(-t-butylperoxy)diisopropylbenzene, 2,5-bis(t-butylperoxy)2,5-dimethylhexane and t-butyl perbenzoate.

In addition to the aforementioned components, the compositions of this invention may also contain other additives such as diluents, levelling agents, inhibitors, pigments and the like.

Sometimes it may be desirable to add a diluent to the ester-containing organosilicon compounds of this invention having aliphatic unsaturation in order to aid in their application to a substrate. If an inert organic solvent is employed, it must be evaporated from the coating; therefore, it is preferred that a radiation reactive diluent be used such as an acrylate ester or a methacrylate ester. Other examples of reactive diluents are ethyl acrylate, n-amyl acrylate, benzyl acrylate, cyclohexyl acrylate, 2-(N-methylcarbamoyloxy)ethylacrylate, diethylaminoethyl acrylate, 2-ethoxyethylacrylate, n-lauryl acrylate, n-octyl acrylate, octadecyl acrylate, the corresponding methacrylates and/or polyacrylates such as trimethylolpropane triacrylate, 1,6-hexanediol diacrylate and pentaerythritol triacrylate. The diluent can be employed at a concentration of from about 0.001 to about 30 weight percent based on the total weight of the radiation polymerizable composition.

The compositions of this invention are applied to a substrate as a coating by any conventional means known in the art such as by roll coating, coating with the aid of a doctor blade, brushing, spraying or dipping the substrate in the coating composition. While paper is one of the most commonly employed substrates, the compositions of this invention can be applied to any substrate such as, for example, glass, steel, aluminum, polyester, woven glass fibers, non-woven glass fibers, non-woven fabrics, optic fibers, as conformal coatings for electronic circuit boards, photo-resist coatings, and as paper coatings.

The amount of radiation polymerizable composition applied to the substrate varies depending on the properties desired in the release coating, the radiation source used, and the composition used. In preparing paper release coatings, generally it has been found that coating weights of from about 0.6 to 2.6 grams per square meter of coated substrate are quite satisfactory.

The radiation polymerizable composition which has been applied to the substrate can be polymerized by exposure to known forms of ionizing or actinic non-ionizing radiation. Suitable forms of radiation include ultraviolet light, electron beam, X-ray, gamma ray and beta-ray sources. The equipment for generating these forms of energy is known in the art. Polymerization may be carried out in atmospheric air or in an inert atmosphere such as nitrogen or argon. The time required to polymerize the coating varies with such factors as the particular composition used, the type and wavelength of the radiation source, the concentration of photosensitizer and the thickness of the coating. It is, however, generally quite short, that is, less than about 10 seconds.

Specific embodiments of this invention are further illustrated in the following examples in which all parts are by weight unless otherwise specified.

EXAMPLE 1

To a flask equipped with a mechanical stirrer, thermometer and reflux condenser are added 82.2 parts of 3-chloropropylmethyl-dimethylpolysiloxane copolymer containing 0.77 percent chloride; 1.9 parts of acrylic acid; 1.6 parts of anhydrous trisodium phosphate; 10 parts of N-methyl pyrrolidone; 3.8 parts of potassium iodide and 0.001 parts of p-methoxyphenol, then heated to about 150° C. for 30 hours and then cooled. The resultant yellow liquid is filtered. The filtrate is vacuum stripped up to about 170° C. at less than 2 torr, yielding about 60 parts of a clear, yellow liquid. Nuclear Magnetic Resonance analysis indicates about 95 mole percent ester formation. The compound formed has a ratio of acrylate groups to dimethylsiloxy groups of 1:63.

EXAMPLE 2

The procedure of Example 1 is repeated, except that 2.3 parts of methacrylic acid are substituted for 1.9 parts of acrylic acid. Nuclear Magnetic Resonance analysis indicates about 94 mole percent ester formation. The compound formed has a ratio of methacrylate groups to dimethylsiloxy groups of 1:64.

Comparison Example V$_1$

The procedure of Example 1 is repeated, except that the potassium iodide is omitted. Nuclear Magnetic Resonance analysis indicates only slight ester formation and that essentially no reaction occurs.

EXAMPLE 3

The procedure of Example 1 is repeated, except that 300 parts of a 3-chloropropylmethyl-dimethylpolysiloxane copolymer containing 0.55 percent chloride; 4 parts of acrylic acid; 9.3 parts of potassium iodide; 5.9 parts of sodium carbonate; 35.5 parts of N-methyl pyrrolidone and 0.3 parts of p-methoxyphenol are added to the flask. The contents of the flask are heated for about 15 hours at about 150° C. and then cooled. About 120 parts of heptane are added and the resultant yellow mixture is filtered. The filtrate is vacuum stripped up to about 170° C. at less than 2 torr, yielding a clear, pale yellow fluid having a viscosity of about 250 mPa.s at 25° C. Nuclear Magnetic Resonance analysis of the fluid indicates the formation of an acryloyloxypropylmethyl-dimethylpolysiloxane copolymer.

EXAMPLE 4

The procedure of Example 3 is repeated, except that 300 parts of a 3-chloropropylmethyl-dimethylpolysiloxane copolymer containing 0.78 percent chloride; 13.1 parts of potassium iodide; 8.4 parts of sodium carbonate; 14.1 parts of p-tertbutylbenzoic acid and 37.3 parts of N-methyl pyrrolidone are added to the flask. The reactants are heated for about 30 hours at 150° C. and then purified in accordance with the procedure described in Example 3. A clear, pale yellow oil having a viscosity of 95 mPa.s at 25° C. is obtained. Nuclear Magnetic Resonance analysis indicates the formation of p-tert-butylbenzoyloxypropylmethyl-dimethylpolysiloxane copolymer.

EXAMPLE 5

The procedure of Example 4 is repeated, except that 11.9 parts of hydrocinnamic acid are substituted for the p-tertbutylbenzoic acid. A clear, pale yellow fluid having a viscosity of 790 mPa.s at 25° C. is obtained. Nuclear Magnetic Resonance analysis indicates the formation of a hydrocinnamoyloxypropylmethyl-dimethylpolysiloxane copolymer.

EXAMPLE 6

The procedure of Example 3 is repeated, except that 1000 parts of a 3-chloropropylmethyl-dimethylpolysiloxane copolymer containing 0.68 percent of chloride; 19.8 parts of methacrylic acid; 38.1 parts of potassium iodide; 24.1 parts of sodium carbonate; 120 parts of N-methyl pyrrolidone and 0.12 parts of p-methoxyphenol are added to the flask. A clear, pale yellow fluid having a viscosity of 471 mPa.s at 25° C. is obtained. Nuclear Magnetic Resonance analysis of the fluid indicates the formation of a methacryloyloxypropylmethyl-dimethylpolysiloxane copolymer.

EXAMPLE 7

The procedure of Example 3 is repeated, except that 300 parts of a chloropropylmethyl-dimethylpolysiloxane copolymer containing 1.37 percent chloride; 15.5 parts of benzoic acid; 23 parts of potassium iodide; 14.6 parts of sodium carbonate; and 39 parts of N-methyl pyrrolidone are added to the flask. A clear, pale yellow fluid having a viscosity of 843 mPa.s at 25° C. is obtained. Nuclear Magentic Resonance analysis indicates the formation of benzoyloxypropylmethyl-dimethylpolysiloxane copolymer.

EXAMPLE 8

The procedure of Example 7 is repeated, except that 20.6 parts of cinnamic acid are substituted for the benzoic acid. A clear, pale yellow product having a viscosity of about 7000 mPa.s at 25° C. is obtained. Nuclear Magnetic Resonance analysis of the product indicates the formation of a cinnamoyloxypropylmethyl dimethylpolysiloxane copolymer.

EXAMPLE 9

The procedure of Example 3 is repeated, except that 300 parts of a 3-chloropropylmethyl-dimethylpolysiloxane copolymer containing 2.17 percent chloride; 49.4 parts of o-benzoylbenzoic acid; 36 parts of anhydrous trisodium phosphate; 36.5 parts of potassium iodide and 43 parts of N-methyl pyrrolidone are added to the flask. A clear, pale yellow fluid having a viscosity of 626 mPa.s at 25° C. is obtained. Nuclear Magnetic Resonance analysis indicates the formation of o-benzoylbenzoyloxypropylmethyl-dimethylpolysiloxane copolymer.

EXAMPLE 10

The procedure of Example 9 is repeated, except that 15.8 parts of acrylic acid are substituted for the o-benzoylbenzoic acid and 0.3 parts of p-methoxyphenol are added. A clear, pale yellow fluid having a viscosity of 211 mPa.s at 25° C. is obtained. Nuclear Magnetic Resonance analysis indicates the formation of acryloyloxypropylmethyl-dimethylpolysiloxane copolymer.

EXAMPLE 11

The procedure of Example 1 is repeated, except that 120 parts of an omega-3-chloropropyldimethylpolysiloxane containing 0.95 percent chloride, 7.2 parts of acrylic acid, 29.2 parts of anhydrous trisodium phosphate, 140 parts of N-methyl pyrrolidone, 29.6 parts of potassium iodide and 0.001 parts of p-methoxy phenol are added to a flask and heated to about 150° C. for about 40 hours. The contents of the flask are cooled to room temperature and the resultant opaque yellow liquid is filtered. The filtrate is vacuum stripped through a wiped film still at 150° C. at less than 1 torr yielding about 85 parts of acryloxypropyldimethylpolysiloxane having a ratio of acrylate groups to dimethylsiloxy groups of about 1:61.

EXAMPLE 12

The procedure of Example 11 is repeated, except that 136.5 parts of a hydrolyzate of 3-chloropropylmethyldichlorosilane, 100 parts of acrylic acid, 101 parts of triethylamine, 168.1 parts of potassium iodide and 750 parts of N-methyl pyrrolidone are used. A yellow liquid product is obtained. Nuclear Magnetic resonance analysis shows that it contains about 0.9 acrylate groups per methyl group bonded to silicon.

EXAMPLE 13

The procedure of Example 1 is repeated, except that 198.5 parts of 3-chloropropyltrimethoxysilane, 101 parts of triethylamine, 1000 parts of acrylic acid, 82 parts of potassium iodide and 10 parts of dimethylformamide are added to a flask and refluxed for about 24 hours, then cooled and filtered. The filtrate is then vacuum stripped at 35° to 40° C. for about three hours at about 1 torr. Nuclear Magnetic Resonance and gas chromatography analyses indicate that acryloxypropyltrimethoxysilane is obtained in about 89 percent purity.

What is claimed is:

1. An improved process for preparing ester-containing organosilicon compounds by reacting a chloro-organosilicon compound with a carboxylic acid or an alkali metal salt of a carboxylic acid, the improvement which comprises conducting the reaction in the presence of a promoting solvent and a catalyst selected from the group consisting of an alkali metal halide, an ammonium halide, a tertiary amine halide and a quaternary ammonium halide, in which the halide is selected from the group consisting of iodide and bromide.

2. The improved process of claim 1, wherein the alkali metal halide is an alkali metal iodide.

3. The improved process of claim 1, wherein the alkali metal halide is an alkali metal bromide.

4. The improved process of claim 2, wherein the alkali metal iodide is potassium iodide.

5. The improved process of claim 3, wherein the alkali metal bromide is potassium bromide.

6. The improved process of claim 1, wherein the carboxylic acid is reacted with the chloro-organosilicon compound in the presence of a hydrogen acceptor.

7. The improved process of claim 6, wherein the hydrogen acceptor is selected from the group consisting of an amine, alkali metal carbonates, alkali metal bicarbonates, alkali metal phosphates, ammonium carbonates, ammonium bicarbonates and ammonium phosphates.

8. The improved process of claim 6, wherein the hydrogen acceptor is an amine.

9. The improved process of claim 1, wherein the catalyst is present in an amount of from 0.001 to about 3 equivalents of catalyst per equivalent of chlorine present in the organosilicon compound.

10. The improved process of claim 1, wherein the promoting solvent is N-methyl-2-pyrrolidone.

* * * * *